United States Patent
Pan et al.

(10) Patent No.: US 10,433,750 B2
(45) Date of Patent: Oct. 8, 2019

(54) METHOD FOR GENERATING ELECTROCARDIOGRAM FOR IDENTIFYING A PERSON AND METHOD FOR IDENTIFYING A PERSON USING THE ELECTROCARDIOGRAM

(71) Applicant: INDUSTRY-ACADEMIC COOPERATION FOUNDATION CHOSUN UNIVERSITY, Gwangju (KR)

(72) Inventors: Sung-Bum Pan, Gwangju (KR); Gyu-Ho Choi, Gwangju (KR); Hae-Min Moon, Gwangju (KR); Youn-Tae Kim, Daejeon (KR)

(73) Assignee: INDUSTRY-ACADEMIC COOPERATION FOUNDATION CHOSUN UNIVERSITY, Gwangju (KR)

( * ) Notice: Subject to any disclaimer, the term of this patent is extended or adjusted under 35 U.S.C. 154(b) by 213 days.

(21) Appl. No.: 15/391,457

(22) Filed: Dec. 27, 2016

(65) Prior Publication Data
US 2018/0168472 A1    Jun. 21, 2018

(30) Foreign Application Priority Data
Dec. 21, 2016    (KR) .................. 10-2016-0175716

(51) Int. Cl.
*A61B 5/0456*    (2006.01)
*A61B 5/04*    (2006.01)
(Continued)

(52) U.S. Cl.
CPC ........ *A61B 5/0456* (2013.01); *A61B 5/04017* (2013.01); *A61B 5/117* (2013.01); *A61B 5/7203* (2013.01)

(58) Field of Classification Search
USPC .................................................. 600/508, 521
See application file for complete search history.

(56) References Cited

U.S. PATENT DOCUMENTS

2004/0138572 A1*   7/2004   Thiagarajan ............. A61B 7/04
                                                                600/508

FOREIGN PATENT DOCUMENTS

| JP | 2016-59771 A | 4/2016 |
|----|---|---|
| KR | 10-2008-0088226 A | 10/2008 |
| KR | 10-2016-0026496 A | 3/2016 |

OTHER PUBLICATIONS

Korean Office Action dated Mar. 7, 2018, issued to Korean Application No. 10-2016-0175716.
(Continued)

*Primary Examiner* — Nicole F Lavert
(74) *Attorney, Agent, or Firm* — Stein IP, LLC

(57) ABSTRACT

Disclosed are a method for generating an electrocardiogram for personal identification and a method for identifying a person using the electrocardiogram. The electrocardiogram generation method generates a normalized electrocardiogram by extracting single-cycle electrocardiogram signals meaningful for personal identification from an electrocardiogram of a person and by connecting the extracted single-cycle electrocardiogram signals arranged in temporal order. Therefore, the electrocardiogram generation method dramatically increases identification accuracy in personal identification.

10 Claims, 8 Drawing Sheets

(51) Int. Cl.
*A61B 5/00* (2006.01)
*A61B 5/117* (2016.01)

(56) References Cited

OTHER PUBLICATIONS

Korean Office Action dated Oct. 22, 2018, issued to Korean Application No. 10-2016-0175716.

* cited by examiner

[FIG. 1]
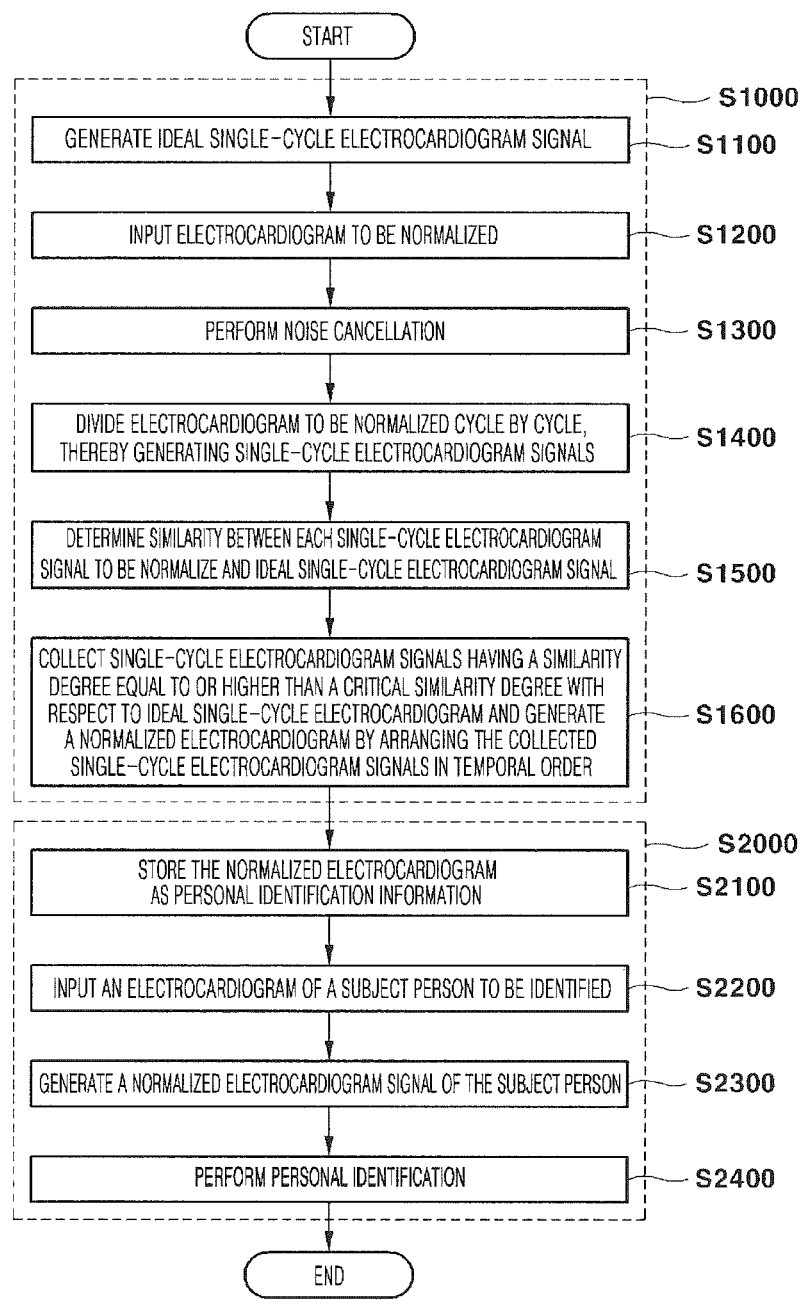

[FIG. 2]

| ITEMS | P WAVE | | Q WAVE | | R WAVE | | S WAVE | | T WAVE | |
|---|---|---|---|---|---|---|---|---|---|---|
| | AMPLITUDE(V) | TIME POSITION | AMPLITUDE(V) | TIME POSITION | AMPLITUDE(V) | TIME POSITION | AMPLITUDE(V) | TIME POSITION | AMPLITUDE(V) | TIME POSITION |
| 1 | 0.025 | 18 | -0.855 | 32 | 2.675 | 42 | -0.415 | 45 | -0.065 | 76 |
| 2 | 0.025 | 20 | -0.195 | 33 | 1.365 | 44 | -0.665 | 39 | 0.155 | 74 |
| 3 | 0.245 | 22 | -0.835 | 31 | 3.165 | 39 | -0.415 | 42 | -0.015 | 73 |
| 4 | 0.115 | 24 | -0.185 | 42 | 1.815 | 45 | -0.965 | 48 | -0.055 | 72 |
| 5 | 0.005 | 16 | -0.565 | 38 | 1.345 | 37 | -0.685 | 46 | 0.395 | 75 |
| 6 | 0.005 | 19 | -0.395 | 34 | 1.535 | 36 | -0.575 | 44 | 0.235 | 77 |
| 7 | -0.175 | 18 | -0.695 | 33 | 3.015 | 38 | -1.015 | 45 | 0.675 | 70 |
| 8 | 0.075 | 17 | -0.615 | 36 | 2.895 | 44 | -0.215 | 43 | 0.365 | 78 |
| 9 | -0.07511 | 21 | -0.2071 | 37 | 0.6142 | 40 | -1.269 | 44 | 0.3537 | 74 |
| 10 | 0.015 | 20 | -0.065 | 38 | 1.415 | 36 | -0.515 | 43 | -0.035 | 72 |
| 11 | 0.155 | 16 | -0.215 | 37 | 2.675 | 34 | -0.935 | 41 | -0.035 | 74 |
| 12 | -0.015 | 22 | -0.735 | 39 | 0.585 | 39 | -0.515 | 47 | 0.115 | 75 |
| 13 | 0.145 | 23 | -0.105 | 28 | 1.755 | 39 | -0.405 | 44 | 0.305 | 76 |
| 14 | 0.005 | 20 | -0.175 | 32 | 0.825 | 33 | -0.405 | 38 | 0.205 | 73 |
| 15 | 0.04437 | 21 | -0.145 | 36 | 1.253 | 41 | -0.6903 | 40 | 0.08449 | 71 |
| 16 | -0.135 | 16 | -0.335 | 37 | 2.335 | 42 | -1.645 | 42 | 0.875 | 74 |
| 17 | 0.035 | 20 | -0.085 | 33 | 1.395 | 40 | -0.165 | 43 | 0.375 | 70 |
| 18 | 0.025 | 24 | -0.175 | 35 | 0.795 | 34 | -0.175 | 41 | -0.005 | 78 |
| AVERAGE | 0.03 | 20 | -0.37 | 35 | 1.75 | 39 | -0.65 | 43 | 0.22 | 74 |

[FIG. 3]
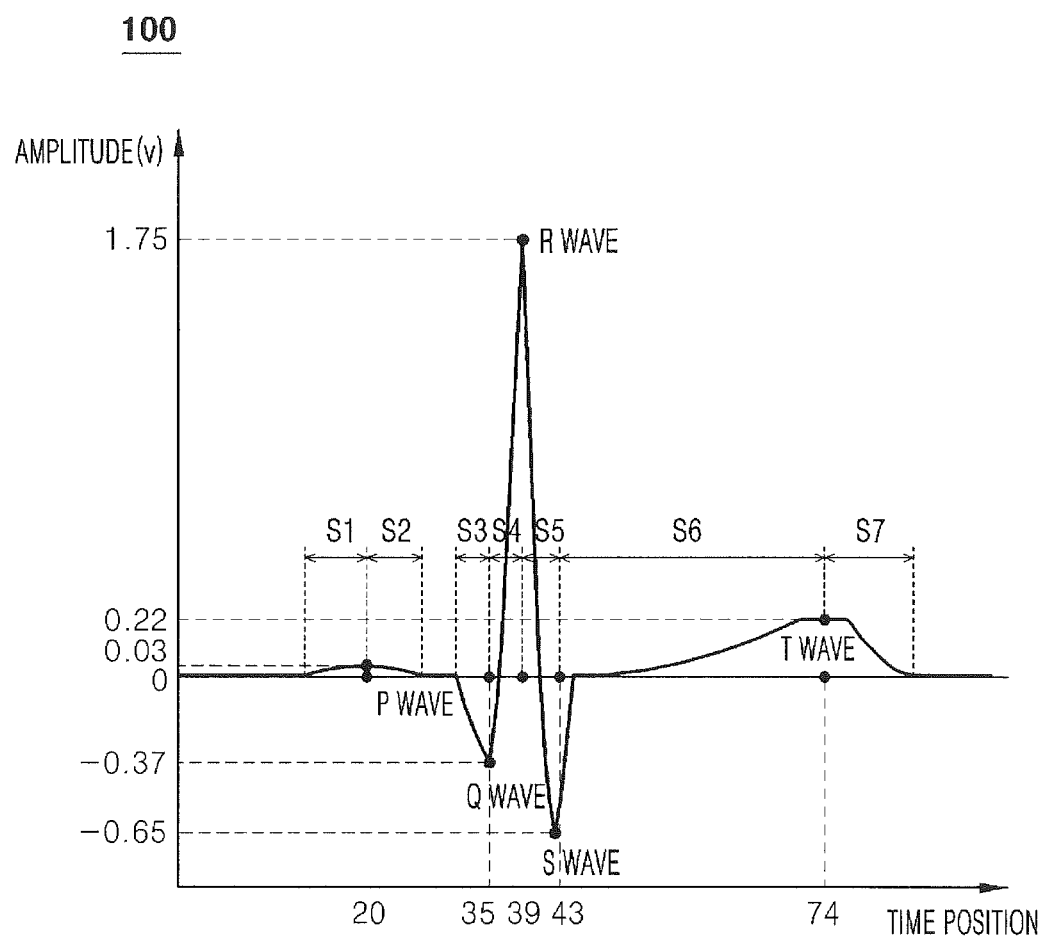

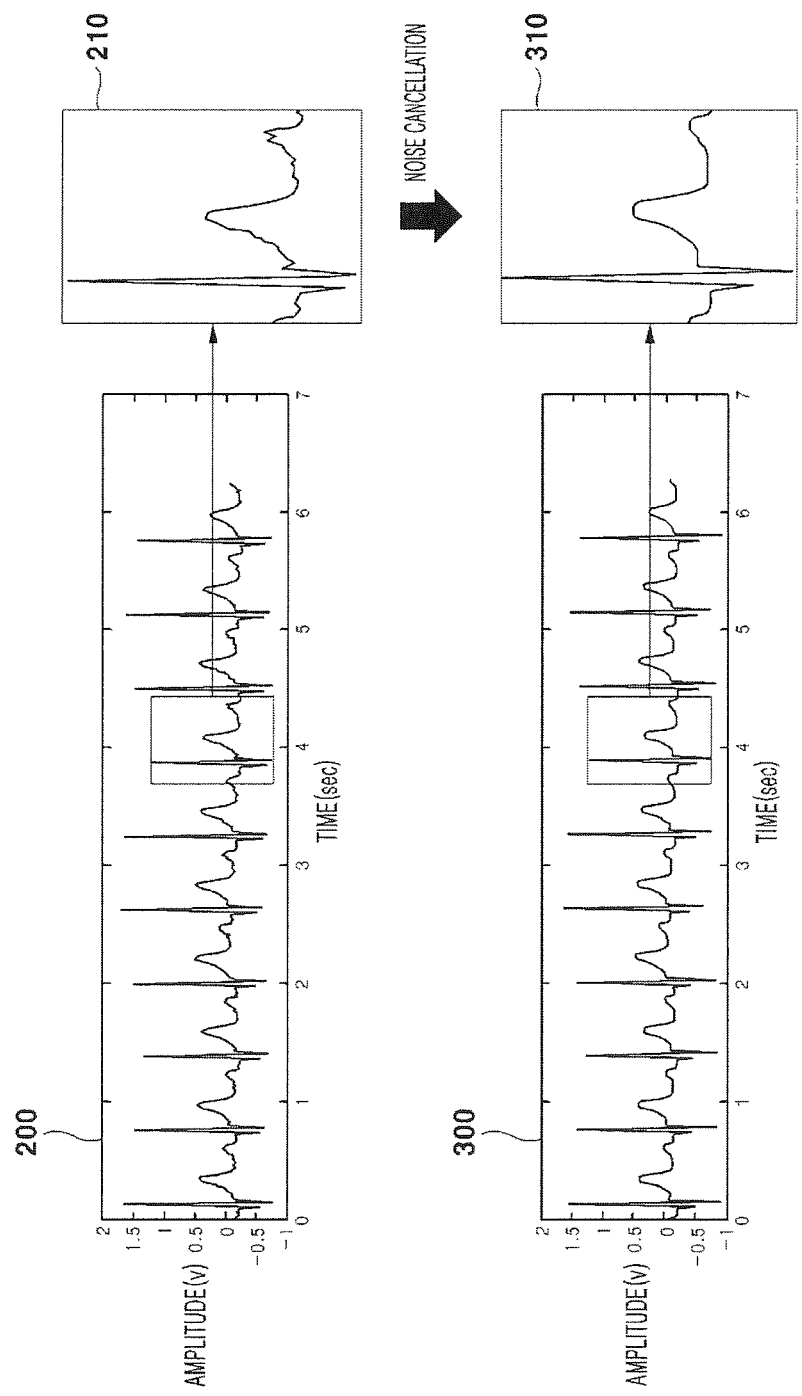
[FIG. 4]

[FIG. 5]
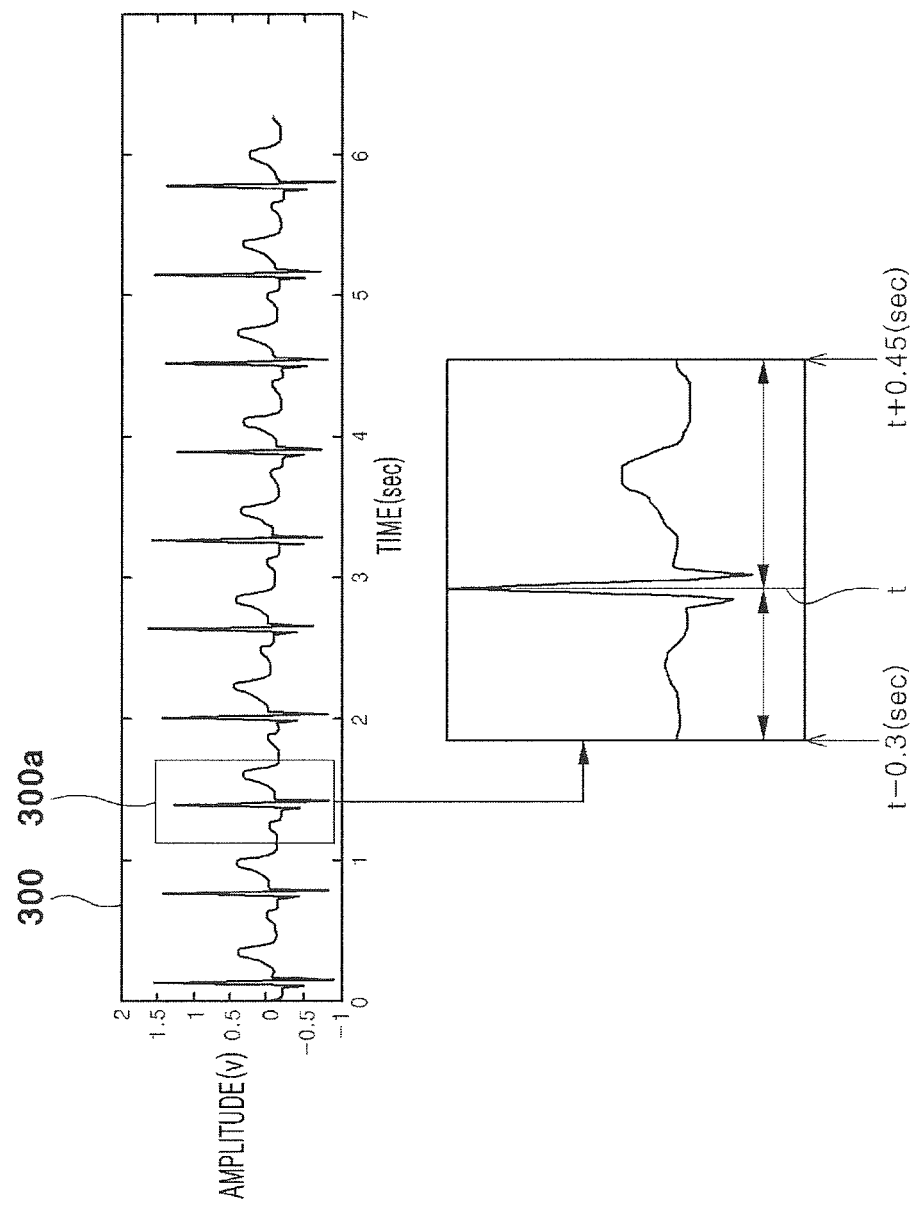

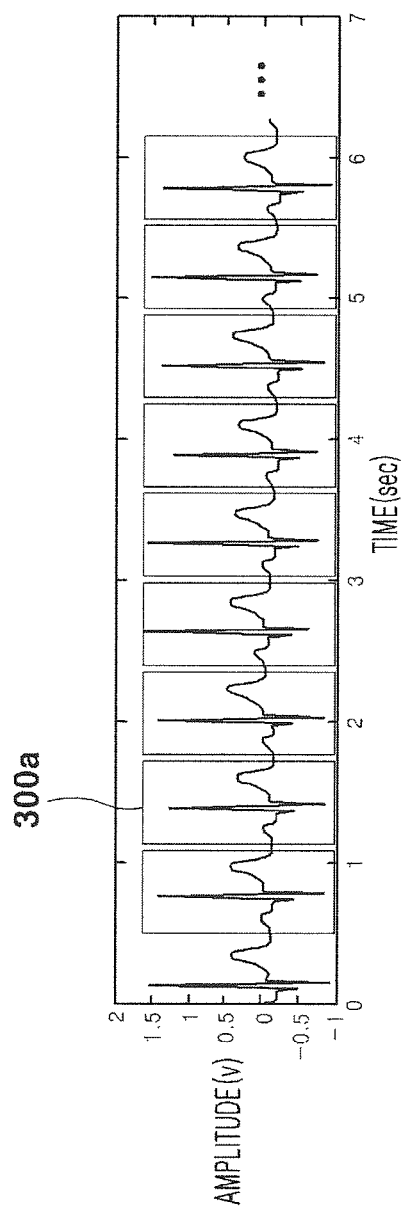
[FIG. 6]

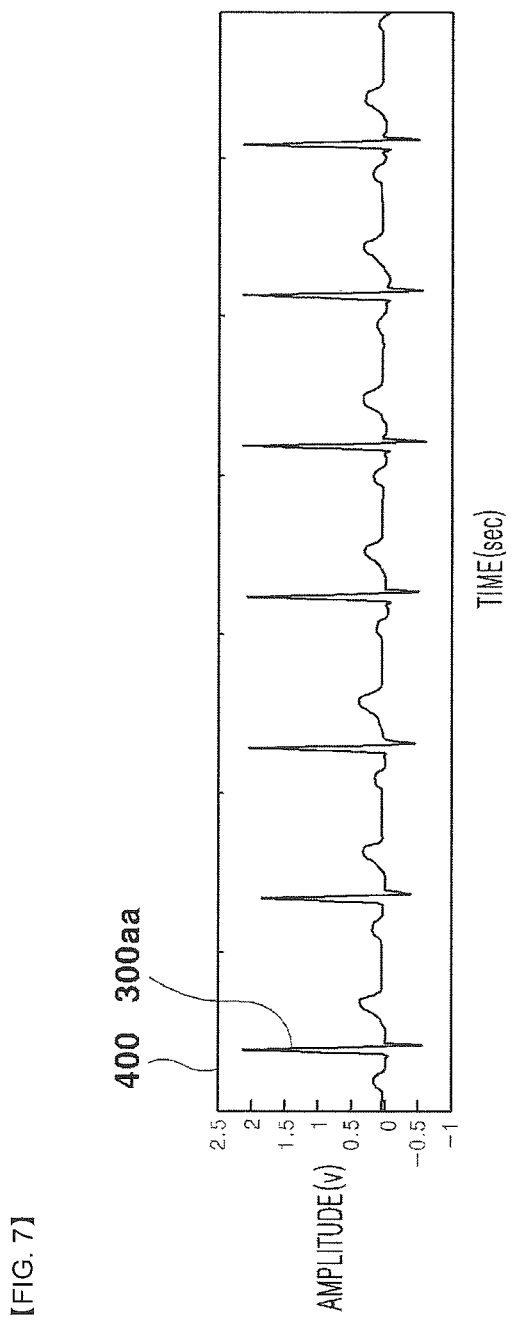
[FIG. 7]

[FIG. 8]
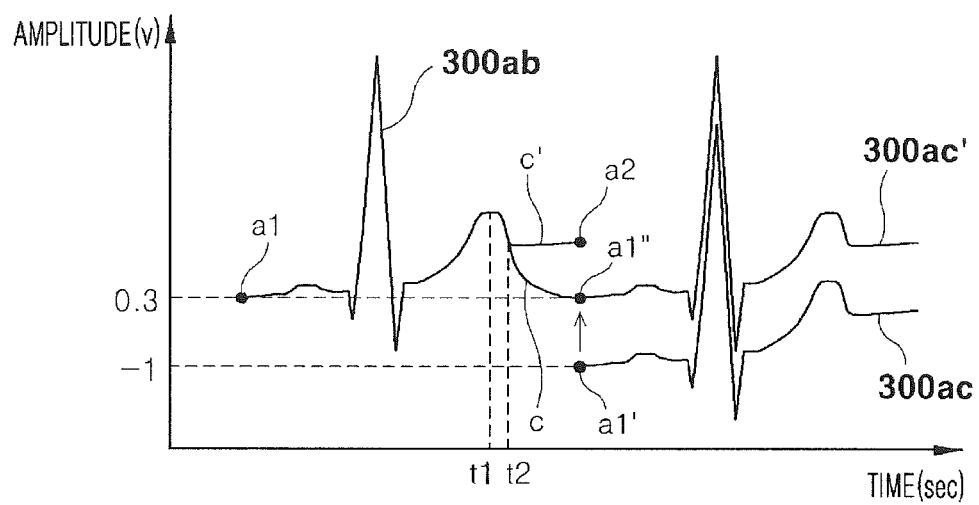

METHOD FOR GENERATING ELECTROCARDIOGRAM FOR IDENTIFYING A PERSON AND METHOD FOR IDENTIFYING A PERSON USING THE ELECTROCARDIOGRAM

CROSS-REFERENCE TO RELATED APPLICATIONS

This application claims the benefit of priority to Korean Patent Application No. 10-2016-0175716 filed Dec. 21, 2016, which is hereby incorporated by reference in its entirety into this application.

BACKGROUND OF THE INVENTION

1. Field of the Invention

The present invention relates a method for generating an electrocardiogram for personal identification and a method for identifying a person using the electrocardiogram. More particularly, the present invention relates to an electrocardiogram generation method for generating a normalized electrocardiogram by extracting multiple single-cycle electrocardiograms that are meaningful for identification and connecting the multiple single-cycle electrocardiograms arranged in temporal order, and also relates to a personal identification method using the normalized electrocardiogram as personal identification information, thereby dramatically increasing an identification rate.

2. Description of the Related Art

Personal identification is broadly used in daily life or in industries in which a password is required. That is, it is conducted for personal authentication when a person wants to have access to buildings, banking systems, or smart electronic devices in which security is a critical issue.

Conventional personal identification methods include a face recognition method, a fingerprint recognition method, and an iris recognition method. Those methods extract characteristics of a person from a facial image, a fingerprint, or an iris image of a person, obtained with the use of an optical sensor of a camera to identify the person.

These conventional personal identification methods utilizing a facial image, a fingerprint, or an iris image have disadvantages. Namely, these methods are vulnerable to a variety of security issues because facial images, fingerprints, or iris images of the absent or the deceased can be used for illegal authentication. Moreover, it is difficult to identify a person in real time using those methods because those methods require processing a large amount of data.

As a solution to this problem, Korean Patent No. 10-0946766 discloses the construction of a personal identification device for identifying a person by using electrocardiogram data.

This personal identification device utilizing electrocardiogram data has an advantage that only an interested person can be authenticated because the electrocardiogram of a person cannot be reproduced or duplicated by other people.

However, a person's electrocardiogram is likely to include abnormal signals when function of the heart or the number of heartbeats is abnormal. In this case, it is difficult to differentiate P, Q, R, S, and T waves from each other, which deteriorates accuracy of personal identification.

SUMMARY OF THE INVENTION

Accordingly, the present invention has been made keeping in mind the above problems occurring in the related art, and the present invention is intended to propose a method for generating an electrocardiogram by extracting multiple single-cycle electrocardiograms that are meaningful for personal identification and by connecting the multiple single-cycle electrocardiograms arranged in temporal order to generate a normalized electrocardiogram, and also to propose a method for identifying a person using the normalized electrocardiogram as personal identification information, thereby increasing accuracy of personal identification.

In order to accomplish the above object, the present invention provides a method (also, referred to as "electrocardiogram generation method") for generating an electrocardiogram, the electrocardiogram generation method including: storing an ideal single-cycle electrocardiogram (hereinafter, referred to as "registered electrocardiogram signal"); inputting an electrocardiogram to be normalized (hereinafter, referred to as "sample electrocardiogram signal"); comparing each cycle of the electrocardiogram (hereinafter, referred to as single-cycle electrocardiogram signal) of the sample electrocardiogram signal with the registered electrocardiogram signal and extracting single-cycle electrocardiogram signals (hereinafter, referred to as "permissible electrocardiogram signals") having a similarity degree equal to or higher than a critical similarity degree with respect to the registered electrocardiogram signal; and collecting the permissible electrocardiogram signals to generate a normalized electrocardiogram and storing the normalized electrocardiogram.

In the preferred embodiment, the electrocardiogram generation method may further include filtering out baseline drift noise or power line interference noise from the sample electrocardiogram signal, wherein the filtering is performed after the inputting of the sample electrocardiogram signal.

In the preferred embodiment, the registered electrocardiogram signal may be obtained by calculating average amplitudes and time positions of P, Q, R, S, and T waves of electrocardiograms stored in a standard electrocardiogram database.

In the preferred embodiment, the similarity degree may be calculated using Euclidean distance.

In the preferred embodiment, the normalized electrocardiogram may be generated by arranging the permissible electrocardiogram signals in temporal order and connecting the permissible electrocardiogram signals to each other.

In the preferred embodiment, values amplitudes of the permissible electrocardiogram signals are adjusted such that values of the initial amplitudes of all of the permissible electrocardiogram signals become equal to each other and such that a value of a last amplitude of a preceding permissible electrocardiogram signal becomes equal to a value of an initial amplitude of a current permissible electrocardiogram signal.

In the preferred embodiment, the adjusting of the values of the amplitudes of the permissible electrocardiogram signals such that the value of the last amplitude of the preceding permissible electrocardiogram signal becomes equal to the value of the initial amplitude of the current electrocardiogram signal may include: detecting a peak amplitude of T wave of the preceding electrocardiogram signal; detecting a second time position at which a gradient of amplitude of the preceding electrocardiogram signal is steepest after a first time position at which the peak amplitude of T wave is detected; and connecting an amplitude at the second time position within the preceding permissible electrocardiogram signal and the initial amplitude of the current permissible electrocardiogram signal, with a curve line consisting of amplitudes calculated according to a predetermined quadratic equation.

In the preferred embodiment, the baseline drift noise and the power line interference noise may be filtered out by a band pass filter.

In order to accomplish the objects of the present invention, according to another aspect, there is provided a computer program stored in a recording medium, the computer program being associated with a computer to implement the electrocardiogram generation method.

In order to accomplish the objects of the present invention, according to a further aspect, there is provided a method (also, referred to as "personal identification method") for identifying a person using an electrocardiogram, the personal identification method including: generating a normalized electrocardiogram (hereinafter, referred to as "first personal identification information) of each person through the method of Claim 1, and then storing the first personal identification information in a database; inputting an electrocardiogram signal of a subject person to be identified; generating a normalized electrocardiogram signal (hereinafter, referred to as "second personal identification information) of the subject person through the method of Claim 1; and performing personal identification by comparing the first personal identification information with the second personal identification information.

In order to accomplish the objects of the present invention, according to a yet further aspect, there is provided a computer program stored in a recording medium, the computer program being associated with a computer to implement the personal identification method.

According to the present invention, the electrocardiogram generation method and the personal identification method using the normalized electrocardiogram generated through the electrocardiogram generation method have advantages that will be explained below. According to the present invention, abnormal cycles of an electrocardiogram that include abnormal amplitudes or from which it is difficult to differentiate among P, Q, R, S, and T waves are removed, and only normal cycles of the electrocardiogram meaningful for personal identification are extracted to generate a normalized electrocardiogram. Since only the normalized electrocardiogram is used for personal identification, it is possible to increase accuracy in personal identification.

BRIEF DESCRIPTION OF THE DRAWINGS

The above and other objects, features and other advantages of the present invention will be more clearly understood from the following detailed description taken in conjunction with the accompanying drawings, in which:

FIG. 1 is a flowchart illustrating an electrocardiogram generation method for generating a normalized electrocardiogram, and a personal identification method, according to one embodiment of the present invention;

FIG. 2 is a table illustrating the structure of a standard electrocardiogram database used to generate an ideal single-cycle electrocardiogram used in the electrocardiogram generation method according to the embodiment of the present invention;

FIG. 3 is a diagram illustrating the waveform of an ideal single-cycle electrocardiogram used in the electrocardiogram generation method according to the embodiment of the present invention;

FIG. 4 is a diagram describing a noise cancellation process to remove noise from an electrocardiogram to be normalized, the process being included in the electrocardiogram generation method according to the embodiment of the present invention;

FIG. 5 is a division process to divide an electrocardiogram into single-cycle electrocardiograms used to normalize the electrocardiogram, the process being included in the electrocardiogram generation method according to the embodiment of the present invention;

FIG. 6 is a diagram illustrating a state in which an electrocardiogram is divided into multiple single-cycle electrocardiograms used to normalize the electrocardiogram, the process being included in the electrocardiogram generation method according to the embodiment of the present invention;

FIG. 7 is a diagram illustrating a normalized electrocardiogram generated through the electrocardiogram generation method according to the embodiment of the present invention; and FIG. 8 is a diagram illustrating a process of arranging and connecting single-cycle electrocardiograms, the process being included in the electrocardiogram generation method according to the embodiment of the present invention.

DESCRIPTION OF THE PREFERRED EMBODIMENTS

Unless otherwise defined, all terms including technical and scientific terms used herein have the same meaning as commonly understood by ordinary people. It will be further understood that terms, such as those specially defined by the applicant of the present application, should be interpreted as having a meaning that is consistent with their meaning in the context of the relevant art and the present disclosure, and will not be interpreted in an idealized or overly formal sense.

Hereinafter, the technical configuration of the present invention will be described with reference to preferred embodiments illustrated in the accompanying drawings.

However, the present invention is not limited to the preferred embodiments described herein but can be embodied in different forms. Throughout the drawings, like reference numbers refer to like elements.

According to one embodiment of the present invention, when using an electrocardiogram for personal identification, a method for generating an electrocardiogram (hereinafter, also referred to as electrocardiogram generation method) eliminates abnormal single-cycle electrocardiogram signals that include abnormal amplitudes or in which it is difficult to differentiate P, Q, R, S, and T waves from each other because the abnormal single-cycle electrocardiogram signals cannot be used for personal identification. The electrocardiogram generation method collects only normal single-cycle electrocardiogram signals that can be used for personal identification to generate a normalized electrocardiogram, thereby increasing an identification rate in personal identification.

A personal identification method according to one embodiment of the present invention performs personal identification using the normalized electrocardiogram generated through the electrocardiogram generation method according to the embodiment of the present invention.

The electrocardiogram generation method and the personal identification method according to the embodiments of the present invention are substantially executed by a computer. To this end, a computer program is stored in a computer, the computer program instructing the computer to execute the electrocardiogram generation method and the personal identification method according to the embodiments of the present invention.

The computer is a computing device in broad terms, and includes a smart electronic device, an embedded system, etc. that can perform image processing, as well as a generally-known personal computer.

The computer program may be provided in the form of a computer program stored in an independent recording medium, wherein the recording medium may be a dedicated storage device specially designed for the present invention or may be a recording medium that is well-known to those ordinarily skilled in the art of computer software.

For example, the recording medium may be a hardware device specially constructed to store and execute program instructions or commands singly or in combination. Examples of the recording medium may include: an electromagnetic medium such as hard disk, floppy disk, or magnetic tape; an optical recording medium such as compact disk (CD) or digital versatile disk (DVD); a magneto-optical recording medium; and a memory device such as ROM, RAM, or flash memory.

In addition, the computer program may be a program involving any one component of program instructions or commands, local data files, and local data structure. The computer program may be machine codes derived by a compiler, or codes that are written in any programming language to be executed by a computer with the aid of an interpreter.

Hereinafter, an electrocardiogram generation and personal identification method according to one embodiment of the present invention will be described with reference to FIG. 1.

With reference to FIG. 1, an electrocardiogram generation and personal identification method according to one embodiment of the present includes an electrocardiogram generation method S1000 for generating a normalized electrocardiogram used as personal identification information and a personal identification method S2000 for performing personal identification using the normalized electrocardiogram.

The electrocardiogram generation method S1000 includes Step S1100 in which an ideal single-cycle electrocardiogram signal (hereinafter, referred to as "registered electrocardiogram signal") that is one cycle of an electrocardiogram is obtained.

The registered electrocardiogram signal is a criterion to eliminate abnormal single-cycle electrocardiogram signals that are not meaningful for personal identification and are likely to cause errors in personal identification, from an electrocardiogram of a person.

The registered electrocardiogram signal is generated by calculating averages of amplitudes and time positions of P, Q, R, S and T waves of electrocardiograms stored in a standard electrocardiogram database.

Specifically, the standard electrocardiogram database used in the embodiment of the present invention is MIT-BIH ECG (provided by Physionet). FIG. 2 is a table showing an average amplitude and an average time position of each of P, Q, R, S, and T waves for electrocardiogram data of 18 people. To obtain the data in FIG. 2, electrocardiograms of 18 people stored in the standard electrocardiogram database are retrieved, and a single-cycle electrocardiogram signal in which P, Q, R, S, and T waves are conspicuously discriminated from each other by eye is selected from each of the electrocardiograms of the 18 people.

Each of the selected single-cycle electrocardiogram signals consists of 95 data items that are amplitudes detected at 95 time positions within the period of one cycle of an electrocardiogram. With reference to Table 2, for P wave, the average peak amplitude and the average time position at which the peak amplitude is detected are 0.03 V and 20. For Q wave, the average amplitude and the time position thereof are −0.37 V and 35. For R wave, the average amplitude and the time position thereof are 1.75 V and 39. For S wave, the average amplitude and the time position thereof are −0.65 V and 43. For T wave, the average amplitude and the time position thereof are 0.22 V and 74.

In addition, to create an ideal single-cycle electrocardiogram signal, data items (amplitudes) for time positions at which the average amplitude is not 0 V are generated according to Equation 1. Thus, a registered electrocardiogram signal 100 shown in FIG. 3 is generated.

Herein, in Equation 1, "i" means the value of a time position.

For a first half section S1 of P wave, $$\text{amplitude}=-1/1200(i-7)^2+0.03(i=13,\ldots,19)$$

For a second half section S2 of P wave, $$\text{amplitude}=-1/1200(i-1)^2+0.03(i=21,\ldots,27)$$

For a first half section S3 of Q wave, $$\text{amplitude}=-1/10 i(i=32,\ldots,34)$$

For a second half section S4 of Q wave, $$\text{amplitude}=-1/10(i)^2-0.47(i=35,\ldots,39)$$

For a first half section S5 of S wave, $$\text{amplitude}=-1/10(i-4)^2-0.65(i=41,\ldots,44)$$

For a second half section S6 of S wave, $$\text{amplitude}=-1/3330(i)^2(i=46,\ldots,72)$$

For a second half section S7, $$\text{amplitude}=-1/300(i-9)^2(i=76,\ldots,84) \quad \text{Equation 1}$$

For example, when i=32, the data item for i=32 belongs to data within the first half section S3 of Q wave and the amplitude at the time position i=32 has a value of 3.2 V that is calculated from −(1/10)×32.

Next, at Step S1200, a person's electrocardiogram signal 200 (hereinafter, referred to as "sample electrocardiogram signal") to be normalized is input.

Next, the sample electrocardiogram signal is pre-processed.

The pre-processing includes Step S1300 in which noise cancellation is performed with respect to the sample electrocardiogram signal and Step S1400 in which the noise-cancelled sample electrocardiogram signal is divided into single-cycle electrocardiogram signals, in which each single-cycle electrocardiogram signal includes a P, Q, R, S, and T wave.

Specifically, the noise cancellation (Step S1300) is to remove base line drift noise and power line interference noise included in the sample electrocardiogram signal.

According to the present invention, base line drift noise occurring at 0.01 Hz or lower and power line interference noise occurring at 45 Hz or higher are removed using a band pass filter.

After the base line drift noise and power line interference noise are removed, median filtering is performed to smooth the sample electrocardiogram signal.

FIG. 4 illustrates the electrocardiogram signal 200 including noise and an electrocardiogram signal 300 from which noise is removed. With reference to FIG. 4, a single-cycle electrocardiogram signal 310 obtained after the noise cancellation is performed has less noise and is smoother than a single-cycle electrocardiogram signal 210 including noise.

Next, at Step S1400, the sample electrocardiogram signal is divided into single-cycle electrocardiogram signals.

FIG. 5 shows a process of dividing the sample electrocardiogram signal 300 into single-cycle electrocardiogram signals 300*a*. According to the present invention, a Pantomkins algorithm is used in this process. That is, first, a time position t at which the peak amplitude of R wave occurs is detected, and a signal occurring for 0.3 seconds before the occurrence of the peak amplitude of R wave and for 0.45 seconds after the occurrence of the peak amplitude of R wave is selected as the single-cycle electrocardiogram signal 300*a*.

After the peak amplitudes of R waves in the sample electrocardiogram signal 300 are detected, the sample electrocardiogram signal 300 is divided into many single-cycle electrocardiogram signals 300*a* as shown in FIG. 6.

Alternatively, the detection of the peak amplitudes of R waves of the single-cycle electrocardiogram signals 300*a* can be performed based on other known algorithms instead of the Pan-tomkins algorithm.

Next, each of the single-cycle electrocardiogram signals 300*a* is compared with the registered electrocardiogram signal 100, and a similarity degree between them is calculated. The single-cycle electrocardiogram signals 300 having a similarity degree equal to or higher than a critical similarity degree are extracted and these signals are called "permissible electrocardiogram signals".

In the present invention, Euclidean distance is used to calculate the similarity degree. In addition, the single-cycle electrocardiogram signals having a similarity degree of 95% or higher are classified as permissible electrocardiogram signals.

Next, a normalized electrocardiogram signal is generated from the permissible electrocardiogram signals.

In this way, abnormal single-cycle electrocardiogram signals in which abnormal amplitudes are included or in which the pattern of P, Q, R, S, and T waves is irregular are removed.

FIG. 7 shows a normalized electrocardiogram signal 400. The normalized electrocardiogram signal 400 is generated by connecting the permissible electrocardiogram signals 300*aa* arranged in temporal order.

Therefore, the present invention has an advantage that it is possible to increase identification accuracy by removing an abnormal portion of an electrocardiogram that obstructs personal identification.

In addition, when arranging the permissible electrocardiogram signals 300*aa* in temporal order, amplitudes of the permissible electrocardiogram signals 300*aa* have to be adjusted such that initial amplitudes of all the permissible electrocardiogram signals are equal to each other, and the initial amplitude of a current permissible electrocardiogram signal is equal to the last amplitude of the preceding permissible electrocardiogram signal.

A method of connecting two permissible electrocardiogram signals to each other will be described with reference to FIG. 8. First, two permissible electrocardiogram signals 300*ab* and 300*ac* are arranged in temporal order such that the initial amplitudes thereof are positioned on the same amplitude value line in an amplitude-time graph.

That is, any one of the two permissible electrocardiogram signals 300*ab* and 300*ac* is shifted up or down so that the initial amplitude a1 (for example 0.3 V) of a permissible electrocardiogram signal 300*ab* at a preceding time (hereinafter, referred to as "preceding permissible electrocardiogram signal") and the initial amplitude a1' (for example, −1 V) of a permissible electrocardiogram signal 300*ac* at a current time (hereinafter, referred to as "current permissible electrocardiogram signal") can be arranged on the same amplitude value line.

When a difference between the initial amplitudes of the preceding permissible electrocardiogram signal 300*ab* and the current permissible electrocardiogram signal 300*ac* is 1.3 V as shown in FIG. 8, the amplitudes of the current permissible electrocardiogram signal 300*ac* are shifted by +1.3 V, thereby generating a shifted current electrocardiogram signal 300*ac'*. That is, the initial amplitude a1' of the current permissible electrocardiogram signal is adjusted to have the same value as the initial amplitude a1 of the preceding permissible electrocardiogram signal 300*ab*.

Conversely, the amplitudes of the preceding permissible electrocardiogram signal 300*ab* may be shifted by −1.3 V so that the initial amplitudes of the two permissible electrocardiogram signals can be equal to each other.

In this way, the amplitudes of all of the permissible electrocardiogram signals are adjusted such that the initial amplitudes thereof can be equal to each other.

Next, the last amplitude a2 of the preceding permissible electrocardiogram signal 300*ab* is adjusted to be equal to the initial amplitude a1" of the shifted current permissible electrocardiogram signal 300*ac'* in the following manner.

That is, after detecting a first time position t1 at which the peak amplitude of T wave of the preceding permissible electrocardiogram signal 300*ab* occurs, a second time position t2 at which the gradient of amplitude of the preceding permissible electrocardiogram signal 300*ab* is steepest is selected. Next, the amplitude at the second time position t2 of the preceding permissible electrocardiogram signal and the initial amplitude a1" of the shifted current permissible electrocardiogram signal 300*ac* are connected with a curve line c that consists of values of amplitudes calculated according to a predetermined quadratic equation.

The amplitudes c' of the preceding permissible electrocardiogram signal 300*ab*, detected after the second time position t2, are all deleted.

The predetermined quadratic equation may be expressed as Equation 2. Constants A, B, and C can be calculated by creating three quadratic equations using two amplitudes detected before the second time position t2 and the initial amplitude a1" of the shifted current permissible electrocardiogram signal 300*ac'*. In Equation 2, i is a time position at which a data item (amplitude) is detected.

$$\text{Amplitude} = Ai^2 + Bi + C \qquad \text{Equation 2}$$

Hereinbefore, the process of obtaining a normalized electrocardiogram has been described. After the normalized electrocardiogram is obtained, it is stored as personal identification information so as to be used in a personal identification process.

Hereinafter, the personal identification method S2000 will be described with reference to FIG. 1. First, at Step S2100, the normalized electrocardiogram 400 is stored as personal identification information (hereinafter, referred to as "first personal identification information").

Next, at Step S2200, an electrocardiogram of a person to be identified is input.

Next, at Step S2300, the inputted electrocardiogram is normalized, thereby generating a normalized electrocardiogram (hereinafter, referred to as "second personal identification information").

The second personal identification information is obtained through the electrocardiogram generation method S1000 that has been described above.

Next, the first personal identification information and the second personal identification information are compared for personal identification.

According to the present invention, when an abnormal amplitude appears in an electrocardiogram of a person due to some functional problems of the heart of the person, an abnormal portion of the electrocardiogram having the abnormal amplitude is removed, and a normalized electrocardiogram is generated using the rest of the electrocardiogram and is used as personal identification information. Therefore, it is possible to dramatically increase identification accuracy in personal identification.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A method for generating an electrocardiogram, the method comprising:
    generating an ideal single-cycle electrocardiogram (hereinafter, referred to as "registered electrocardiogram signal") by calculating averages of amplitudes and time positions of P, Q, R, S and T waves of electrocardiograms of a plurality of persons stored in a standard electrocardiogram database;
    storing the registered electrocardiogram signal;
    inputting an electrocardiogram of a single person to be normalized (hereinafter, referred to as "sample electrocardiogram signal");
    comparing each cycle of the electrocardiogram (hereinafter, referred to as single-cycle electrocardiogram signal) of the sample electrocardiogram signal with the registered electrocardiogram signal and extracting a plurality of single-cycle electrocardiogram signals (hereinafter, referred to as "permissible electrocardiogram signals") from the sample electrocardiogram signal each of which has a similarity degree equal to or higher than a critical similarity degree with respect to the registered electrocardiogram signal; and
    collecting the permissible electrocardiogram signals;
    generating a normalized electrocardiogram using the permissible electrocardiogram signals and storing the normalized electrocardiogram.

2. The method according to claim 1, further comprising:
    filtering out baseline drift noise or power line interference noise from the sample electrocardiogram signal, after performing the inputting of the sample electrocardiogram signal.

3. The method according to claim 1, wherein the similarity degree is calculated using Euclidean distance.

4. The method according to claim 1, wherein the normalized electrocardiogram is generated by arranging the permissible electrocardiogram signals in temporal order and connecting the permissible electrocardiogram signals to each other.

5. The method according to claim 4, wherein values amplitudes of the permissible electrocardiogram signals are adjusted such that values of the initial amplitudes of all of the permissible electrocardiogram signals become equal to each other and such that a value of a last amplitude of a preceding permissible electrocardiogram signal becomes equal to a value of an initial amplitude of a current permissible electrocardiogram signal.

6. The method according to claim 5, wherein the adjusting of the values of the amplitudes of the permissible electrocardiogram signals such that the value of the last amplitude of the preceding permissible electrocardiogram signal becomes equal to the value of the initial amplitude of the current electrocardiogram signal includes:
    detecting a peak amplitude of T wave of the preceding electrocardiogram signal;
    detecting a second time position at which a gradient of amplitude of the preceding electrocardiogram signal is steepest after a first time position at which the peak amplitude of T wave is detected; and
    connecting an amplitude at the second time position within the preceding permissible electrocardiogram signal and the initial amplitude of the current permissible electrocardiogram signal, with a curve line consisting of amplitudes calculated according to a predetermined quadratic equation.

7. The method according to claim 2, wherein the baseline drift noise and the power line interference noise are filtered out by a band pass filter.

8. A non-transitory computer-readable medium storing a computer program, the computer program being associated with a computer to implement the method of claim 1.

9. A method for identifying a person using an electrocardiogram, the method including:
    generating a normalized electrocardiogram (hereinafter, referred to as "first personal identification information) of each person through the method of claim 1, and then storing the first personal identification information in a database;
    inputting an electrocardiogram signal of a subject person to be identified;
    generating a normalized electrocardiogram signal (hereinafter, referred to as "second personal identification information) of the subject person through the method of claim 1; and
    performing personal identification by comparing the first personal identification information with the second personal identification information.

10. A non-transitory computer-readable medium storing a computer program, the computer program being associated with a computer to implement the method of claim 9.

* * * * *